(12) United States Patent
Herschman

(10) Patent No.: US 11,426,500 B2
(45) Date of Patent: Aug. 30, 2022

(54) SYSTEMS AND METHODS FOR REMOVING SPECIFIC IMPURITIES FROM FLUIDS SUCH AS BLOOD USING A NANOTUBE SELECTOR

(71) Applicant: Zvi Herschman, West Hempstead, NY (US)

(72) Inventor: Zvi Herschman, West Hempstead, NY (US)

( * ) Notice: Subject to any disclaimer, the term of this patent is extended or adjusted under 35 U.S.C. 154(b) by 728 days.

(21) Appl. No.: 16/415,678

(22) Filed: May 17, 2019

(65) Prior Publication Data

US 2020/0360585 A1    Nov. 19, 2020

(51) Int. Cl.
| | |
|---|---|
| *A61M 1/16* | (2006.01) |
| *A61F 2/02* | (2006.01) |
| *A61M 1/34* | (2006.01) |
| *B01D 61/42* | (2006.01) |
| *B82Y 30/00* | (2011.01) |
| *B01D 69/04* | (2006.01) |

(52) U.S. Cl.
CPC .......... *A61M 1/1621* (2014.02); *A61F 2/022* (2013.01); *A61M 1/1678* (2013.01); *A61M 1/3417* (2014.02); *A61F 2230/0069* (2013.01); *A61F 2250/0001* (2013.01); *A61F 2250/0023* (2013.01); *A61F 2250/0043* (2013.01); *B01D 61/42* (2013.01); *B01D 61/422* (2013.01); *B01D 69/043* (2013.01); *B82Y 30/00* (2013.01)

(58) Field of Classification Search
CPC .............. A61M 1/1621; A61M 1/1678; A61M 1/3417; A61M 1/34; A61M 1/36; A61F 2/022; A61F 2230/0069; A61F 2250/0001; A61F 2250/0023; A61F 2250/0043; B01D 61/42; B01D 61/422; B01D 69/043; B01D 63/06; B01D 71/021; B82Y 30/00
See application file for complete search history.

(56) References Cited

U.S. PATENT DOCUMENTS

| | | | |
|---|---|---|---|
| 3,697,410 | A | 10/1972 | Johnson et al. |
| 3,994,799 | A | 11/1976 | Yao et al. |
| 5,489,370 | A | 2/1996 | Lomasney et al. |
| 5,776,325 | A | 7/1998 | Partridge |
| 6,086,739 | A | 7/2000 | Hodko |
| 6,284,117 | B1 | 9/2001 | Smolko et al. |
| 6,555,058 | B2 | 4/2003 | Kamibayashi et al. |
| 7,048,856 | B2 | 5/2006 | Fissell, IV et al. |

(Continued)

FOREIGN PATENT DOCUMENTS

| | | |
|---|---|---|
| CN | 101947417 A | 1/2011 |
| CN | 102366713 A | 3/2012 |

(Continued)

OTHER PUBLICATIONS

Israel Patent Office, form PCT/ISA/237, Written Opinion of the International Searching Authority, for PCT/JS2020/031884, dated Jun. 25, 2020.

(Continued)

*Primary Examiner* — Krishnan S Menon

(74) *Attorney, Agent, or Firm* — Wiggin and Dana LLP; Abraham Kasdan; Thomas M. Landman

(57) ABSTRACT

An array of hollow nanotubes is configured and dimensioned to allow impurities to transport through the hollow nanotubes from a first space containing an impurity-laden fluid to a second space where the impurities may be collected for removal, allowing fluids, such as blood, to be purified.

15 Claims, 5 Drawing Sheets

(56) References Cited

U.S. PATENT DOCUMENTS

| | | |
|---|---|---|
| 7,066,900 B2 | 6/2006 | Botto et al. |
| 7,540,963 B2 | 6/2009 | Fissell, IV et al. |
| 7,651,600 B2 | 1/2010 | Han et al. |
| 8,871,074 B2 | 10/2014 | Suh et al. |
| 9,220,829 B2 | 12/2015 | Herschman |
| 10,117,737 B2 | 11/2018 | Herschman |
| 2004/0049288 A1 | 3/2004 | Levin |
| 2004/0124147 A1 | 7/2004 | Fissell, IV et al. |
| 2005/0103622 A1 | 5/2005 | Jha et al. |
| 2006/0027499 A1 | 2/2006 | Ajayan et al. |
| 2006/0073089 A1 | 4/2006 | Ajayan et al. |
| 2006/0240061 A1 | 10/2006 | Atala et al. |
| 2007/0108068 A1 | 5/2007 | Suh et al. |
| 2008/0004712 A1 | 1/2008 | Humes et al. |
| 2008/0051696 A1 | 2/2008 | Curtin et al. |
| 2008/0107739 A1 | 5/2008 | Kraft |
| 2008/0223795 A1 | 9/2008 | Bakajin et al. |
| 2009/0131858 A1 | 5/2009 | Fissell et al. |
| 2009/0218226 A1 | 9/2009 | Coiffic et al. |
| 2010/0100027 A1 | 4/2010 | Schilthuizen et al. |
| 2010/0316694 A1 | 12/2010 | Mousa et al. |
| 2011/0247937 A1 | 10/2011 | Suh et al. |
| 2012/0211367 A1 | 8/2012 | Vecitis |

FOREIGN PATENT DOCUMENTS

| | | |
|---|---|---|
| EP | 2087916 A1 | 8/2009 |
| EP | 2446908 A1 | 5/2012 |
| EP | 2683425 B1 | 2/2017 |
| WO | 2007025104 A2 | 3/2007 |
| WO | 2008075951 A1 | 6/2008 |
| WO | 2008086477 A1 | 7/2008 |
| WO | 2019014633 A1 | 1/2019 |

OTHER PUBLICATIONS

Kevin Bonsor & Jonathan Strickland, "How Nanotechnology Works". HowStuffWorks.com, <"http://science.howstuffworks.com/nanotechnology2.htm/printable">, accessed Dec. 31, 2014.

TheNanoAge. "Carbon Nanotubes". TheNanoAge.com,<"http://www.thenanoage.com/carbon-nanotubes.htm">, accessed Dec. 31, 2014.

Allen R. Nissenson et al., The Human Nephron Filter: Toward a Continuously Functioning, Implantable Artificial Nephron System, May 20, 2005, Blood Purification, vol. 23, pp. 269-274, USA.

H. M. Amasha et al., Implantable Electronic Kidney, IFMBE Proceedings, vol. 5, Track 18, p. 3172, USA.

International Search Report, corresponding to International Application No. PCT/US2012/28018, dated Jun. 19, 2012.

William Fissell, Anna Dubnisheva, Abigail Eldridge, Aaron Fleischman, Andrew Zydney and Shuvo Roy, High-Performance Silicon Nanopore Hemofiltration Membranes, National Institute of Health, J. Membr. Sci. Jan. 5, 2009.

A.T. Conlisk, Subhra Datta, William Fissel and Shuvo Roy, Biomolecular Transport Through Hemofiltration Membranes, National Institute of Health, Ann. Biomed. Eng., Apr. 2009.

Chad D.Vecitis et al., Electrochemical Carbon Nanotube Filter for Adsorption, Desorption, and Oxidation of Aqueous Dyes and Anions, J. Phys. Chem, Feb. 16, 2011, pp. 3621-3629, vol. 115, No. 9.

Supplemental European Search Report in EP Application No. 12755026.7 dated Mar. 11, 2015.

SYSTEMS AND METHODS FOR REMOVING SPECIFIC IMPURITIES FROM FLUIDS SUCH AS BLOOD USING A NANOTUBE SELECTOR

RELATED APPLICATIONS

The present application is related in subject matter to U.S. Pat. Nos. 9,220,829 and 10,117,737, the entire contents of which are hereby incorporated herein by reference.

FIELD OF THE DISCLOSURE

In U.S. Pat. Nos. 9,220,829 and 10,117,737, novel systems and methods were disclosed by the present inventor for selectively removing selected impurities from fluids, including bodily fluids such as blood. In such systems and methods, impurities may be transported into the hollow interiors of arrays of nanotubes through appropriately-sized pores formed in the sidewalls of the nanotubes. The impurities so transported into the interiors of the nanotubes of the array may then be removed as a waste stream. When used to purify blood, the sidewall pores may be specifically sized to allow certain impurities in the blood (typically small to medium-sized molecules) to transport through the sidewall pores in the nanotube walls, while larger essential constituents of the blood that are not impurities, e.g. red blood cells, are blocked. As disclosed therein, such impurity transport may be assisted by applying electric fields in the vicinity of the nanotubes that may be oriented so as to assist in the diffusion of selected impurities across the sidewall pores and into the hollow interiors of the nanotubes.

Building on these prior developments, in this application, additional systems and methods are disclosed that selectively transport specifically-sized impurities present in a fluid (e.g., blood) into the interiors of hollow nanotubes arranged in an array, so that the impurities may be readily separated from the fluid, thereby leaving the remaining fluid in a purified condition.

Accordingly, this disclosure provides additional novel systems and methods for removing undesirable impurities from a fluid, e.g., blood, by using the unique properties of ordered arrays of nanotubes such as, e.g., carbon nanotubes.

BACKGROUND

While the systems and methods disclosed herein may be used to purify various fluids, of specific interest and application is the use of such systems and methods in an artificial kidney capable of purifying blood.

In healthy humans and animals, the kidneys act to purify the blood by effectively removing excess water, salts, toxins, as well as breakdown materials and waste products (e.g., as produced by metabolism) that circulate in the blood.

Sometimes, however, the kidneys may fail to operate effectively for a variety of reasons, including various diseases. In individuals suffering kidney failure, their kidneys do not function properly and naturally produced waste products found in the blood stream are not effectively removed. As a consequence, about 600,000 people in the United States of America, and millions of people worldwide, suffer from kidney failure. This number has been estimated to be increasing at annual rates of about 9%.

Generally speaking, to restore such a patient to close to full health, a kidney transplant is needed. However, the demand for kidney transplants is heavily outnumbered by the limited supply of donor organs. For example, in 2017 there were about 100,000 patients in the United States on waiting lists for a kidney transplant, while less than 20,000 kidney transplants were performed that year.

Even with a kidney transplant, complications such as host rejection and complications from immunosuppressive medications, which may have to be taken for life to prevent rejection, are not uncommon. In addition, graft versus host and transplanted infectious diseases can also develop. As a consequence, in many patients with loss of kidney function (e.g., renal failure), the normal cleaning process performed by the kidneys has to be performed artificially, for example, through external treatments such as dialysis, typically either hemodialysis or peritoneal dialysis.

In hemodialysis, a patient's blood is typically re-routed outside the body to a dialyzer which filters the blood using disposable cartridges that include numerous substantially small, semipermeable, plastic membranes, with varying pore sizes. As blood diffuses through the capillary system of the dialysis cartridge, contaminants are removed from the patient's blood in conjunction with a counter-current flow of a fresh dialysate solution. Toxins in the blood (e.g., salts and various unwanted low molecular weight molecules) preferentially diffuse across these membranes as a result of flow-induced or osmotic pressure differentials, thereby reducing toxin concentrations in the blood. The now-purified blood is then returned to the patient's body, usually via a vein in the arm and/or through the lumen of an inserted catheter.

However, this type of dialysis procedure has many drawbacks. In order to undergo dialysis, patients have to be connected for considerable amounts of time to large and expensive machines. Patients may typically be required to receive dialysis treatments at least three to four times a week, for about three to five hours at a time. Even with such extensive and frequent treatments, dialysis machines may only be about 13% as effective as a fully functional kidney. Unfortunately, the five-year survival rate of patients on dialysis has been estimated to be just 33-35%.

Further, the ability of the dialysis treatment to remove large molecular mass molecules, called middle molecular weight molecules, merely by diffusion across a membrane is very inefficient. When using dialysis, only about 10-40% of such larger molecules may be removed during a given dialysis session. This can lead to a buildup of larger-sized toxins within the patient's blood. Consequently, without removal, these toxins can reach abnormally high concentration levels and can damage the body over time. Some have speculated that inefficient removal of these toxins represents a significant limitation of current renal dialysis technology.

To achieve adequate removal of these toxins, manufacturers and nephrologists have been attempting to increase the surface areas of dialysis membranes and to also prolong dialysis treatment times. However, there are practical limits to increasing the surface areas of dialysis membranes. In addition, increasing the dialysis treatment times adds to the detrimental physical and social side effects of dialysis, by reducing the patient's quality of life and adding to the expense of treatment for people suffering from loss of kidney function.

To overcome these deficiencies, the present invention builds on advances in nanotube fabrication technology to provide novel and efficient approaches for removing undesirable impurities, including the aforementioned toxins, that may be present in a fluid such as blood.

By way of background, the fabrication of carbon nanotubes has been extensively studied in recent years, because they have unique physical and chemical properties that are useful in many applications. Technologies have been developed to efficiently manufacture various types of nanotubes and nanotube arrays. For example, it is now possible to fabricate both single-walled and multi-walled carbon nanotubes using various chemical vapor deposition (CVD) fabrication methods, among other techniques. Significantly, by controlling the process parameters and growth environments, vertically aligned "forests" or arrays of carbon nanotubes can be grown on a substrate for use in various applications and devices.

Appropriate growth conditions and techniques for growing such vertically aligned carbon nanotube arrays have been described in various publications. By way of example, and without limitation, such publications include: (1) "Nickel Overlayers Modify Precursor Gases To Pattern Forests of Carbon Nanotubes," J. Phys. Chem. C 2017.121: 11765-11772, R. Yemini, A. Itzhak, Y. Gofer, T. Sharabani, M. Drela, G. D. Nessim; (2) "Differential preheating of hydrocarbon decomposition and water vapor formation shows that single ring aromatic hydrocarbons enhance vertically aligned carbon nanotubes growth," Carbon, 109 (2016) 727-736, E. Teblum, A. Itzhak, E. Shawat Avraham, M. Muallem, R. Yemini, G. D. Nessim; (3) "Patterning of Forests of Carbon Nanotubes (CNTs) Using Copper Overlayers as Iron Catalyst Deactivators," J. Phys. Chem. C. 120 (2016) 12242-12248, R. Yemini, M. Muallem, T. Sharabani, E. Teblum, Y. Gofer, G. D. Nessim; (4) "Millimeter-Tall Carpets of Vertically Aligned Crystalline Carbon Nanotubes Synthesized on Copper Substrates for Electrical Applications," J. Phys. Chem. C. 118 (2014) 19345-19355, E. Teblum, M. Noked, J. Grinblat, A. Kremen, M. Muallem, Y. Fleger, et al., and (5) "Properties, synthesis, and growth mechanisms of carbon nanotubes with special focus on thermal chemical vapor deposition," Nanoscale. 2 (2010) 1306-1323, Gilbert D. Nessim. The contents of these publications are also incorporated herein by reference.

BRIEF DESCRIPTION OF DRAWINGS

The features and advantages of the present disclosure will be more fully understood with reference to the following description, when taken in conjunction with the accompanying figures, wherein.

DETAILED DESCRIPTION

Figure 1:
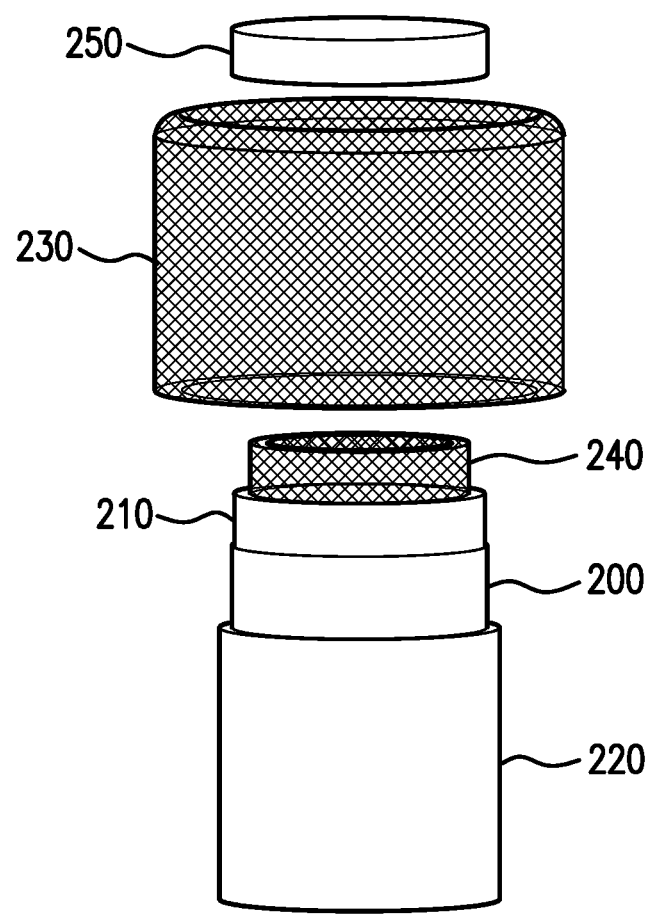
FIG. 1 illustratively depicts an assembly view of an exemplary embodiment of a cylindrical carbon nanotube selector.

The following detailed description is directed to novel systems and methods for removing impurities from fluids such as, for example, blood, by using arrays of aligned hollow nanotubes, e.g., carbon nanotubes, arranged to selectively remove certain impurities from a fluid.

In particular, the nanotubes may be manufactured to have a hollow interior that is dimensioned to selectively permit impurities with a smaller dimension to pass through, while larger-sized constituents of the fluid are blocked from passing through. Such selective removal of impurities based on size is very useful for purifying blood, since typically the impurities that are removed, e.g., by conventional dialysis techniques, are smaller than the key constituents of the blood, e.g., red blood cells.

As described herein, several novel approaches and configurations are disclosed for fabricating such nanotube selectors using arrays of aligned nanotubes that may be fabricated from carbon or other materials.

In exemplary embodiments, the inner diameters of the nanotubes in the nanotube selector can range from about 1 nm (e.g., for single wall semipermeable nanotubes) to about several nanometers (e.g., for multi-wall semipermeable nanotubes). For example, the inner diameter of typical multi-wall hollow nanotubes that are currently available is in the range of about 2 to 6 nanometers (nm). Such diameters are of the same order of magnitude as the size of most single molecules. Comparatively, a single red blood cell has a diameter of about 7,000 nm, while a typical virus measures only about 100 nm in diameter.

In exemplary embodiments, the nanotubes have generally cylindrical shapes that can be several microns to one or more millimeters long with aspect ratios (e.g., length to diameter ratio) in excess of 10,000 or more.

As described in the foregoing references identified herein and known in the art, arrays of vertically aligned nanotubes, e.g., carbon nanotubes are generally grown on flat non-porous substrates that would block the flow of fluids through their hollow interiors. Therefore, to make the hollow interiors of a vertically aligned nanotube array accessible to a fluid undergoing purification, the vertically aligned nanotube array may be removed from the substrate after growth and supported on a substrate, so as to provide for fluid flow through the hollow nanotube interiors.

For example, after growth of the aligned nanotubes, they may be transferred to or otherwise supported by a fluid impermeable support material, so as to leaving their ends open to fluid transport. As one fabrication example, the spaces between the nanotubes may be sealed by, e.g., infiltrating a polymer material between the spaces to form a fluid impermeable polymer support matrix that supports and maintains the alignment of the nanotubes.

Plasma oxidation or other etching processes may be thereafter be employed to remove the original substrate on which the vertically aligned nanotubes were grown, so as to expose the open ends of the hollow nanotubes that were originally attached to the substrate. When this processing is completed, the nanotubes will be supported in the support material, but the ends of the nanotubes will be open and accessible for transport of fluids containing impurities and the like, through the hollow nanotubes, from one side of the support material to the other side.

By using a material, such as flexible polymer matrix, to support the vertically aligned nanotube array, the resulting structure may be wrapped into a cylindrical configuration, generally shown by reference numeral 200 in FIG. 1. As evident, the nanotube array 200 that was generally aligned to a substrate during the growth process, when cylindrically wrapped, will have its nanotubes generally oriented in a radial direction with respect to the center of the cylinder. This is illustrated by the cross-sectional view of FIG. 2 where the diffusion direction depicted by the arrow is in the radially inward direction towards the center of the cylinder, which is on the right side of FIG. 2.

Reverting back to FIG. 1, to provide further structural support for the cylindrical array of now generally radially aligned hollow nanotubes, the layer 200 may be sandwiched between an inner fabric layer 210 and an outer fabric layer 220, both of which may be electrically insulating and sufficiently porous to readily permit impurities that may be present in a fluid circulating in a first space outside the cylindrical assembly to pass through the fabric layers 210 and 220, and flow through the hollow interiors of the nanotubes in layer 200 into a second space internal to the cylindrical assembly.

In addition to providing a porous support for the cylindrical nanotube layer 200, by incorporating inner and outer fabric layers 210, 220 that are electrical insulators, these layers 210, 220 may also act to electrically insulate the nanotube layer 200, which would be electrically conductive in the case where the nanotube layer 200 is made from carbon-based nanotubes.

By way of example, and without limitation, many suitable electrically insulating porous fabrics may be used, such as fiberglass insulation cloth or PTFE fabric (Teflon®), to name but several examples.

As further shown in the exemplary embodiment of FIG. 1, an inner cylindrical metallic mesh 240 is positioned radially interior to the inner cylindrical fabric layer 210, and an outer metallic mesh 230 is positioned to surround the outer fabric layer 220. These metallic meshes, 230, 240 act as further supporting members for the intervening layers 210, 200 and 220 and provide conductive surfaces that are electrically insulated from the nanotubes by the fabric layers 210, 220.

Accordingly, an electrical voltage may be applied between the inner and outer meshes 230, 240 to provide an electric field therebetween that can assist in the transport of impurities through the hollow interiors of the nanotube layer 200, in which the nanotubes are generally aligned in a radial direction perpendicular to the cylinder axis.

The electric field may be generated by an appropriate electrical voltage source to which the metallic meshes 230, 240 are connected by conductive leads (e.g., leads 380, 390 shown in FIG. 3A and discussed below).

Figure 2:
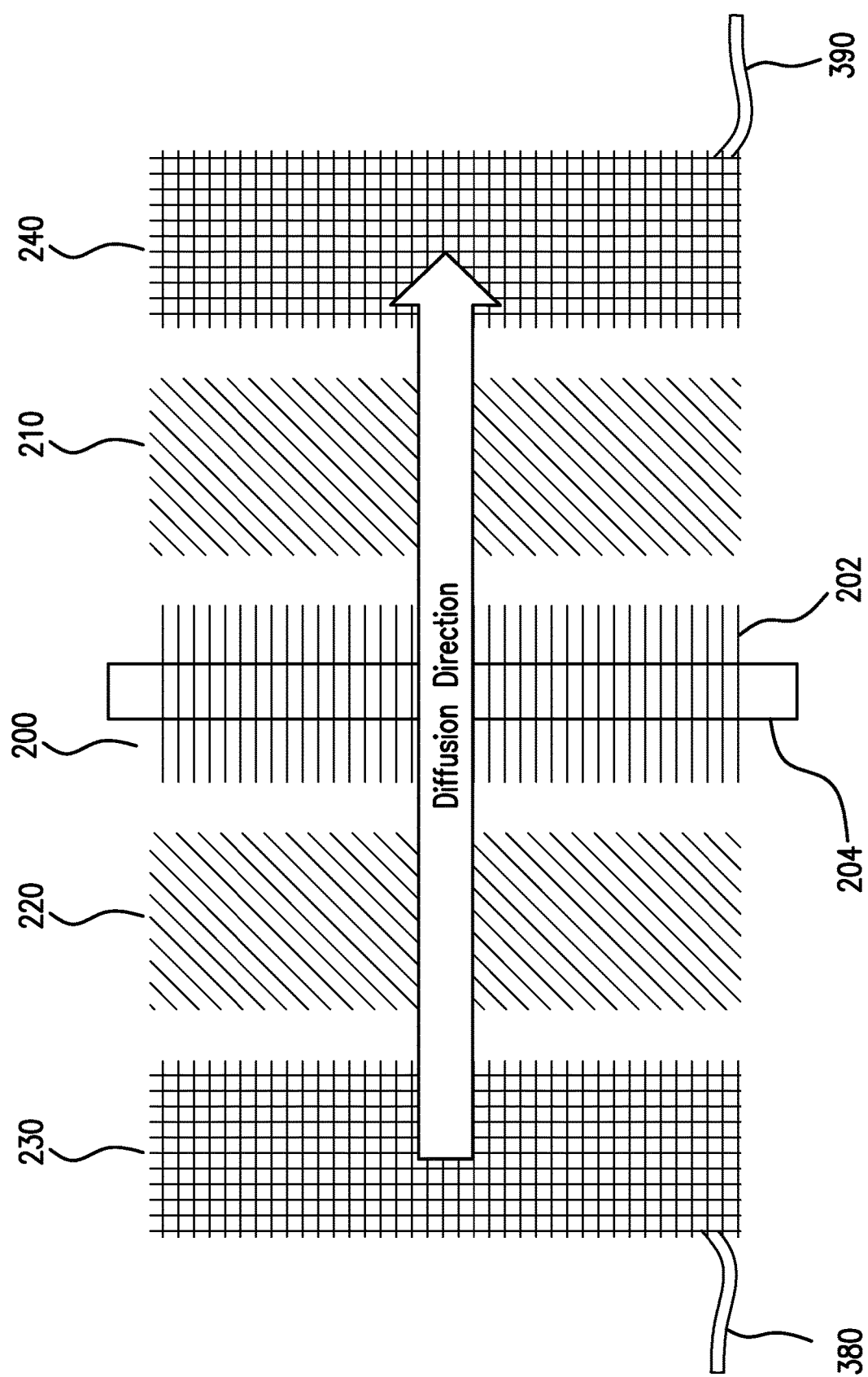
FIG. 2 illustratively depicts a cross-sectional view of the FIG. 1 exemplary embodiment, taken through the center of the cylinder.

A partial cross-sectional view of the FIG. 1 cylindrical nanotube selector assembly is shown in FIG. 2, with the cylindrical outside of the selector assembly being depicted on the left-hand side of FIG. 2. As shown in the FIG. 2 cross-sectional view of the FIG. 1 embodiment, the nanotube array 200 comprises nanotubes 202 that are supported by a support structure 204, such that the ends of the nanotubes are open to receive fluid containing impurities that may be circulating in a first outer space surrounding the cylindrical nanotube selector and permit them to be transported through the hollow nanotubes into a second interior space formed, at least in part by the inner portion of the hollow cylinder, where they may be collected for removal.

Thus, in FIG. 2, impurities present in a fluid that is introduced in a first space surrounding the outside of the nanotube selector assembly will diffuse (in a diffusion direction depicted by the arrow in FIG. 2) through the nanotubes and the various layers of the nanotube selector into a second space formed at least in part by the interior of the cylindrical nanotube selector.

In operation a fluid containing impurities may flow inwardly through the outer mesh 230 and through the relatively large pores in the fabric 220. Impurities in the fluid having sizes that are less than the inner dimensions of the hollow nanotubes, will continue to flow and diffuse into the hollow interiors of the nanotubes in the nanotube layer 200. For example, when fabricated, if the fluid to be purified is blood, the interior lumens of the hollow nanotubes can be dimensioned to pass water and other impurities, while red blood cells and other constituents of the blood, whose dimensions are too large to pass through the interiors of the nanotubes, will be excluded.

In the exemplary embodiment of FIG. 2, upon exiting the nanotube layer 200, the fluid, including impurities with dimensions small enough to pass through the hollow nanotube interiors, will continue to diffuse through the inner fabric 210 and through the inner mesh 240 into the interior space of the nanotube selector assembly, where it may be collected to form a waste stream for removal.

As shown in FIG. 2, conductive leads 380, 390 may be respectively connected to the outer metal mesh 230 and inner metal mesh 240. A voltage source (not shown) can be applied across leads 380 and 390 to generate an electric field for selectively enhancing the diffusion of charged impurities across the nanotube selector assembly.

Referring back to FIG. 1, to complete the nanotube selector assembly, a cap 250 may be positioned on one end of the cylinder so as to cover the interior of the cylinder. The cap 250 prevents fluid in the outer space from entering directly into the interior space of the cylinder, thereby insuring that only impurity-laden fluid that is transported through the hollow nanotubes will enter the interior space. In addition, once the impurity-laden fluid is within the interior space, the cap 250 prevents such fluid from escaping through the top of the cylinder so that it can be collected and/or removed in a waste stream.

In accordance with this exemplary embodiment, fluid that has entered into the interior space of the cylinder is an impurity-laden fluid that has traversed the hollow interiors of the nanotubes in the nanotube layer 200. Such fluid can either be collected by a collection system, e.g., a system including a receptacle placed at the bottom of the interior space of the cylindrical nanotube selector, or may be further channeled to a collection system that includes a waste outlet port for collection as a waste stream.

For example, when the nanotube selector assembly is used as part of an implantable artificial kidney system to purify blood, the impurity-laden fluid could be channeled into a waste stream that would be passed to the body's ureter for excretion through a surgically fabricated structure, as generally discussed and illustrated in U.S. Pat. No. 9,220,929.

As should be evident to workers of skill in the art, once impurities are transported into the interior space of the nanotube selector, the flow of the fluid and the electrical field that may be generated in the vicinity of the nanotube selector will make it improbable for such impurities to diffuse back in the opposite direction, thereby resulting in separation of the impurities in the fluid.

Figure 3A:
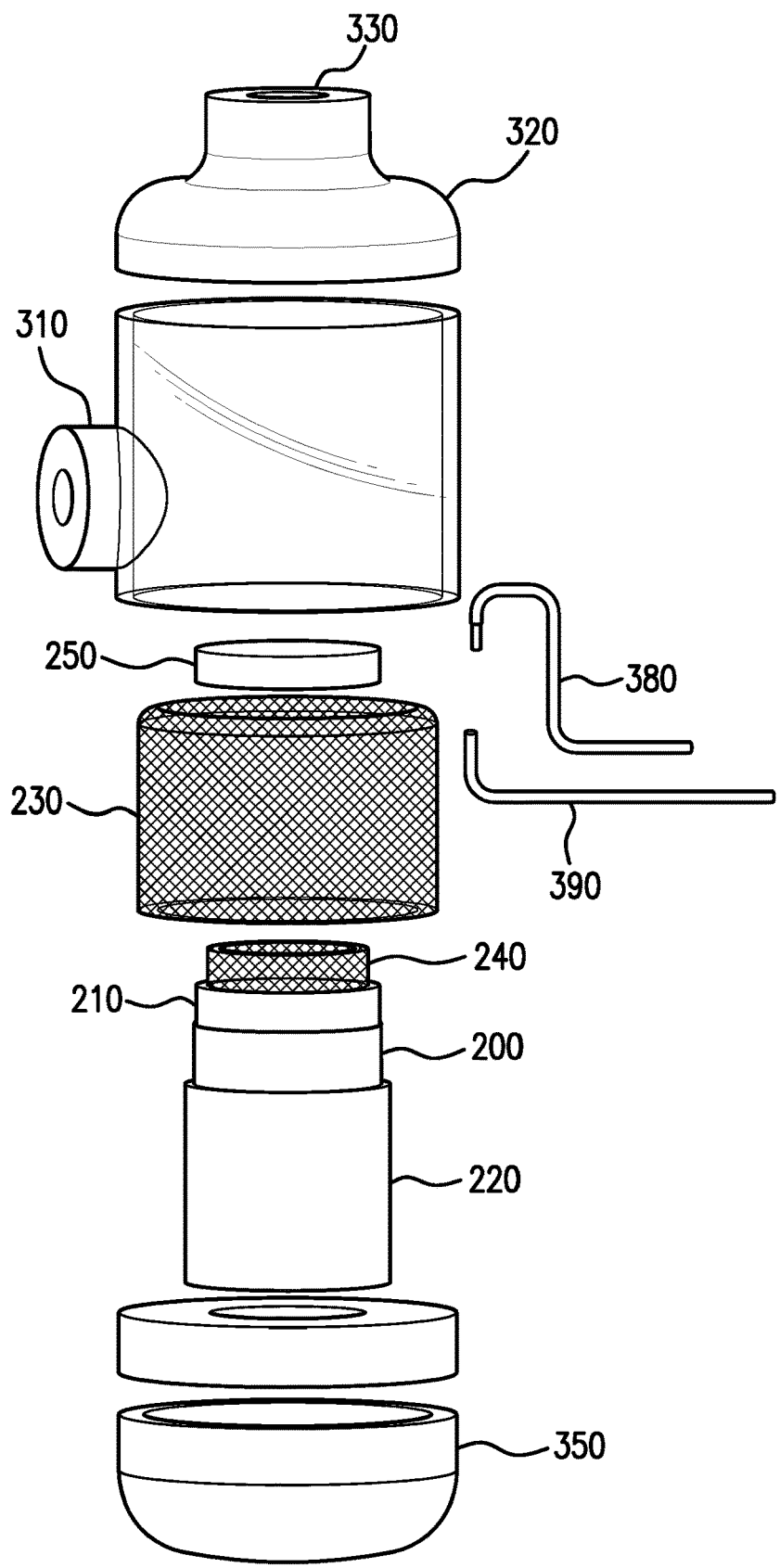
FIG. 3A illustrates an exploded view of a carbon nanotube selector showing one example of how it may be arranged in a housing.
Figure 3B:
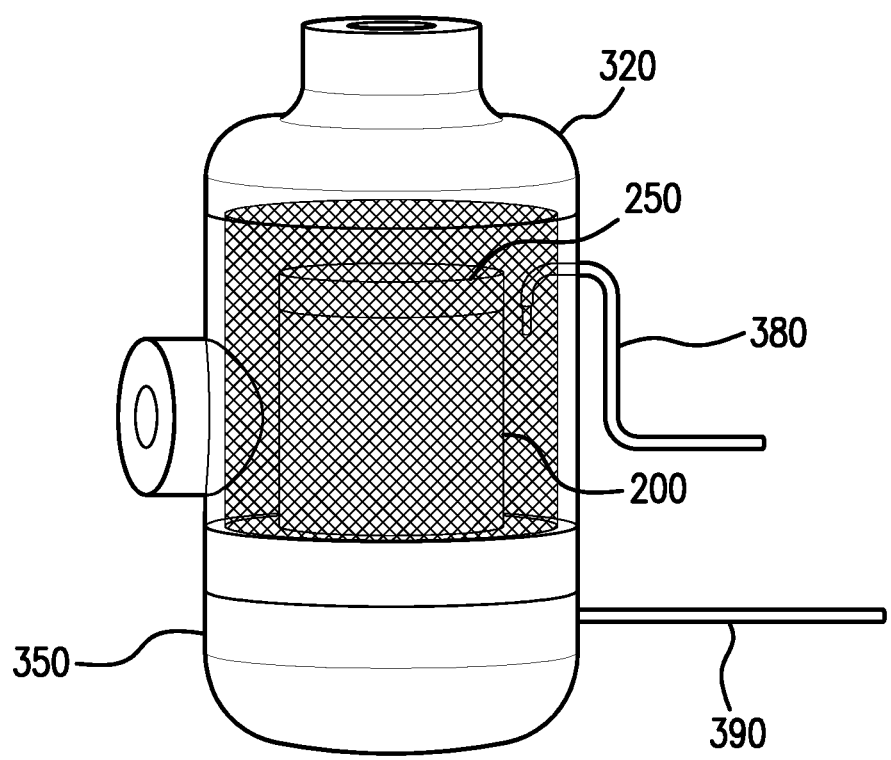
FIG. 3B shows the arrangement of FIG. 3A, after assembly.

The nanotube selector assembly described above, may be assembled into a housing, as shown in the exploded view of FIG. 3A, where like components are labelled with the same reference numerals used in FIG. 1. As shown in FIG. 3A, the components of the nanotube selector may be assembled and enclosed by a housing having a cylindrical portion with a fluid outlet port 310, a top portion 320 having a fluid inlet port 330, and a bottom portion 350 in which the impurities that pass through the nanotube selector may be collected. FIG. 3B shows a fully assembled view in which electrode wires 380 and 390, which in operation would be connected to a voltage source, are arranged to pass through the housing for respective connections to the outer and inner metal meshes 230, 240.

When assembled as shown in FIG. 3B, fluid to be purified may flow into the container at the top through the fluid inlet port 330 and out through the outlet port 310. As evident, fluid leaving the outlet port 310 may be recirculated back to the inlet port 330 in multiple passes and be further purified during each pass through the selector. In each such pass, impurity-laden fluid that passes through the hollow radially-arranged nanotubes in the nanotube layer and into the center of the selector may be collected in the bottom portion 350 of the housing or diverted into a waste stream.

Figure 4A:
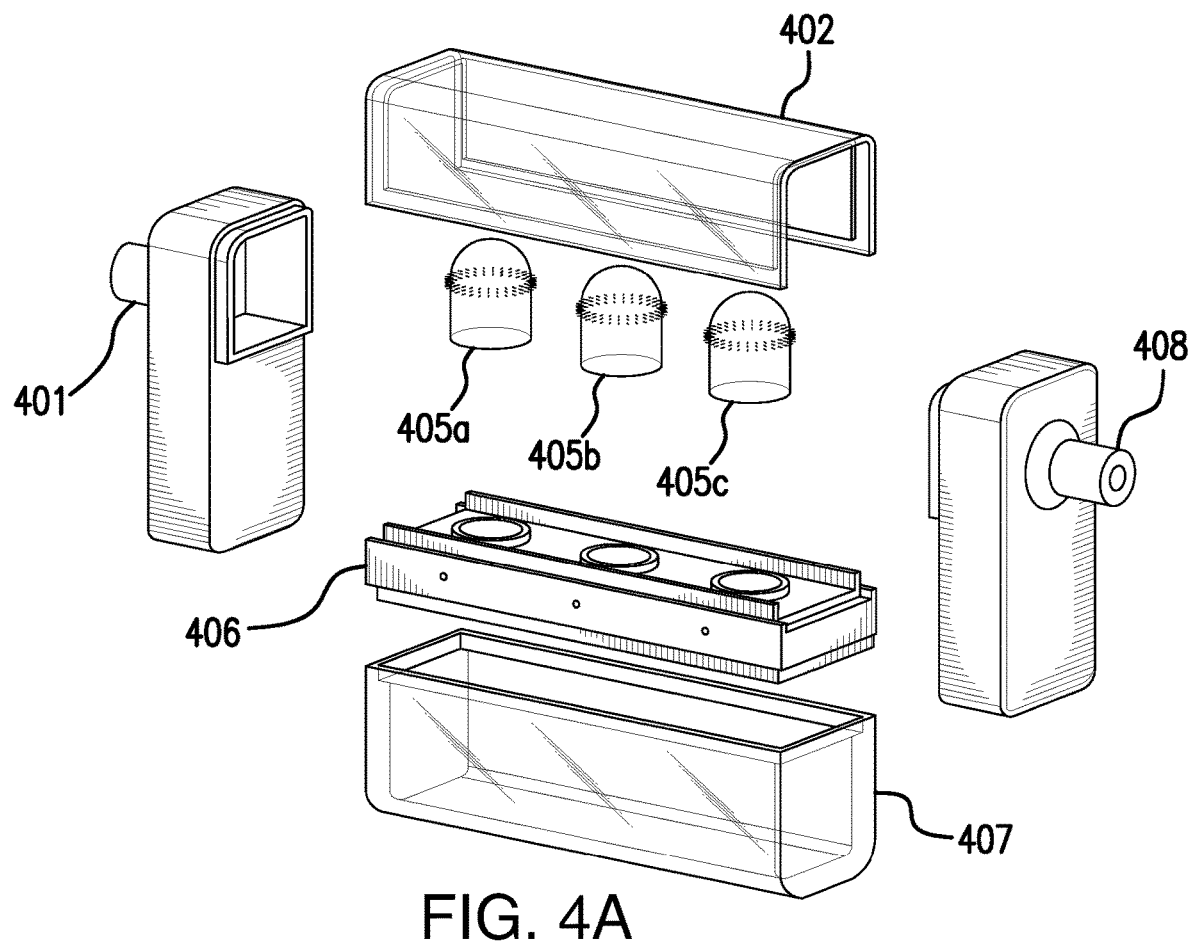
FIG. 4A illustrates an exploded view of a second embodiment showing an assembly of multiple carbon nanotube selectors.
Figure 4B:
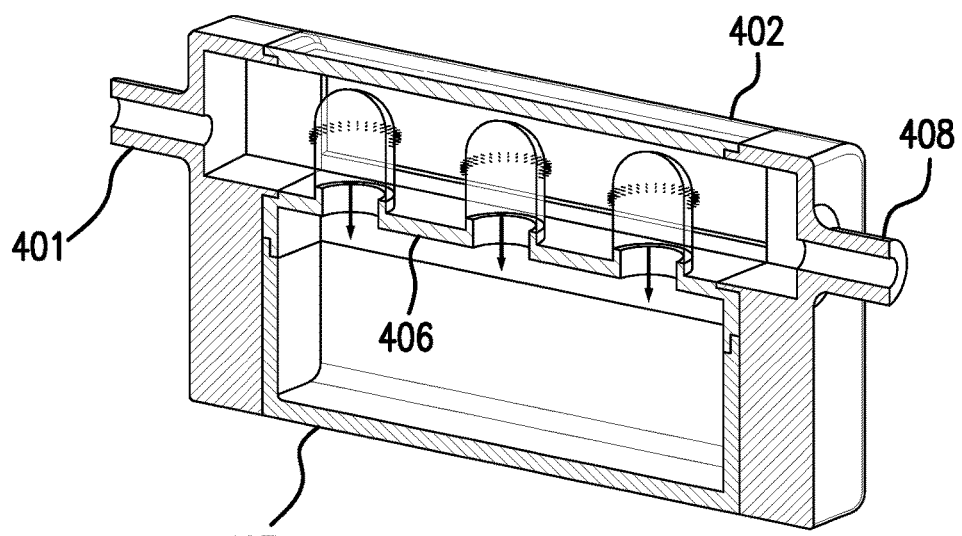
FIG. 4B illustrates a cutaway view of the assembled second embodiment of FIG. 4A.

To increase the efficiency of impurity separation and removal, multiple nanotube selectors may be operated in parallel, as shown in the exemplary embodiment of FIGS. 4A, B, where FIG. 4A shows an exploded view and FIG. 4B shows an assembled view.

With reference to FIG. 4A, multiple nanotube selectors 405a, 405b, and 405c may be assembled into a common housing. Note that in the exemplary FIGS. 4A, B embodiment, the three nanotube selectors 405a, 405b, and 405c are shown to have a domed cap, but are otherwise may each be constructed in substantially the same manner as shown in FIG. 1. Although three selectors are shown, it is contemplated that many such selectors may be arranged to operate in parallel.

As further shown in FIG. 4A, each cylindrical nanotube selector is mounted in a mounting interface portion 406 that allows only impurity-laden fluid that has passed through the nanotube selector and into its inner space to communicate with a collection system such as receptacle 407.

As discussed above with respect to FIG. 1, each nanotube selector 405a, 405b, and 405c includes a radially-arranged array of hollow nanotubes that permits fluid and impurities that are sufficiently small, to flow through the hollow interiors of the nanotubes and into the cylindrical interior space of the nanotube selector, from which the impurity-laded fluid may enter the collection system, such as receptacle 407.

As shown in FIGS. 4A, B, fluid to be purified may enter through an inlet port 401 into a common enclosure 402. The fluid exits through outlet port 408.

Only impurity-laden fluid that passes through the hollow nanotube array in each of the nanotube selectors 405a, 405b, and 405c enters the common collection system, e.g., receptacle 407, from where it may be removed.

Although, the exemplary embodiment of FIGS. 4A, B shows the impurity-laden fluid being collected in a common collection receptacle 407, the common receptacle may be part of a collection system that may be configured to include a waste outlet port from which the impurity-laden fluid may be removed as a waste stream.

Still further, it is also contemplated that the fluid leaving outlet port 408 may be recirculated through appropriate piping and fittings for reentry back into the inlet port 401, so that additional purification of the fluid may occur as the fluid is recirculated through the nanotube selectors in multiple passes. Since a substantially large number of purification passes can be readily implemented by recirculation of the fluid, each single pass may only be required to remove a small amount of impurities.

When the nanotube selector assemblies are used as an artificial kidney, following the purification process, purified blood and contained plasma can be rerouted and/or returned to the patient.

As in the FIG. 1 embodiment, each of the nanotube selectors may have electrodes (not shown in FIGS. 4A, B) attached to the inner and outer metallic meshes and to a voltage source to provide an electric field across the nanotube selector to enhance the diffusion of impurities through the nanotube selector.

It will be understood by those of ordinary skill in that art that the disclosed systems and methods can be used for separating and removing impurities, including charged impurities, and filtering impurities from any type of fluid such as, but not limited to, water, aqueous solutions, non-aqueous solutions, precious material recovery systems, wastewater processing, blood, cerebrospinal fluid, bile, and bio-fluids.

While in a preferred embodiment, the fluid being filtered and/or purified is blood, the foregoing descriptions are in no way meant to be a limitation on the types of fluids that can be purified using the disclosed systems and methods.

Further, when used as artificial kidney system, the nanotubes and/or other materials may be functionalized with specifically selected surfactants and/or anticoagulants selected to prevent blood that contacts their surfaces from coagulating or clotting.

As used herein, "functionalized" (or any version thereof) refers to surface treatments by which specific atomic molecular groups may be attached to alter the specific properties of the nanotubes or structures described herein.

Functionalization can be generally performed by various surface modification techniques such as wet chemistry, or vapor, gas, and/or plasma chemistry, and microwave assisted chemical techniques, to name a few. These techniques utilize surface chemistry to bond desirable materials to surfaces of carbon nanotubes.

When the exemplary embodiments are used in an artificial kidney system, polymers, anticoagulants, and/or other selected molecules may be attached to surfaces of the nanotubes and/or other parts of the assembly.

Anticoagulant molecules (e.g., similar to Heparin or Hirudin) may also be covalently linked to the nanotubes using such known techniques. Once so attached, these anticoagulant molecules help to substantially prevent the blood from clotting.

Further, in exemplary embodiments, the nanotube selector assembly can be fitted to utilize sensors designed to detect the presence of certain impurities. This would allow, for example, the ability to measure concentrations of selected charged species within the incoming blood and/or within the already purified blood and/or within the waste stream, or as may be desired from any combination of these locations. Such sensors may include, by way of example, impurities-specific sensors, ion-specific electrochemical sensors, spectroscopic type sensors, which can communicate signals to suitable microcontrollers.

Such sensors can measure concentrations of selected charged species in either the incoming fluid (before filtration) and/or the outgoing fluid (after filtration). This information, when coupled to appropriate feedback mechanisms, allows regulation of applied potentials across the nanotube selector.

By way of example, the general types of sensors that can be utilized may include, but are not limited to, sensors that can rapidly detect multiple species such as, but not limited to, Na+(aqueous) and K+(aqueous).

Further, the sensors can be designed to communicate their information to a microprocessor for evaluation and response. By way of example, the nanotube selector assembly can utilize such sensors, microprocessors, and/or other devices to control and/or provide feedback by utilizing technologies similar to those used with, for example, pacemakers and spinal cord stimulators.

While carbon-based nanotubes have been widely studied to date and are available in various configurations, it is further contemplated that the foregoing systems and methods may be use nanotube arrays formed from other materials, and should not be understood as being limited to carbon-based nanotube arrays.

Now that exemplary embodiments of the present disclosure have been shown and described in detail, various modifications and improvements thereon will become readily apparent to those skilled in the art, all of which are intended to be covered by the following claims.

What is claimed is:

1. A nanotube selector for separating impurities in a fluid comprising:
    a support material forming at least part of an enclosure separating a first space containing said fluid from a second space, said support material being impermeable to said impurities in said fluid;
    a plurality of hollow nanotubes, each having a first end and a second end, supported by the support material such that their first ends are in the first space and their second ends are in the second space, said hollow nanotubes having interior diameters dimensioned to allow impurities to transport through their hollow interiors from the first space to the second space to be separated from said fluid; and
    first and second electrically conductive materials configured to provide an electric field in the vicinity of the nanotubes when connected to a voltage source, to facilitate transport of said impurities through said hollow nanotubes.

2. The nanotube selector of claim 1, further comprising one or more electrically insulating materials positioned on either side of the support material, wherein said one or more electrically insulating materials is permeable to said fluid and impurities.

3. The nanotube selector of claim 2, wherein said one or more insulating materials is a fabric.

4. The nanotube selector of claim 1 wherein said first electrically conductive material is positioned in the first space adjacent to the support material and said second electrically conductive material is positioned in the second space adjacent to the support material.

5. The nanotube selector of claim 4, wherein the first and second electrically conductive materials are metallic meshes.

6. The nanotube selector of claim 1, wherein:
    the support material is formed into a cylindrical enclosure separating the first space containing fluid external to the cylindrical enclosure from the second space interior to the cylindrical enclosure.

7. The nanotube selector of claim 6, further comprising one or more electrically insulating fluid permeable materials on either side of the support material.

8. The nanotube selector of claim 7, wherein said one or more electrically insulating fluid permeable materials is a porous fabric.

9. The nanotube selector of claim 6, wherein said first and second electrically conductive materials are permeable to said fluid and impurities.

10. A plurality of nanotube selectors in accordance with claim 1, arranged to permit an impurity-containing fluid in a first space to transport in parallel through each of said nanotube selectors, said plurality of nanotube selectors having a common second space for collecting fluid and impurities that have flowed through the hollow nanotubes.

11. A method for purifying a fluid containing impurities, comprising the steps of:
    providing a plurality of hollow nanotubes supported in a support material such that first ends of the hollow nanotubes are open to a first space containing the fluid and second ends of the hollow nanotubes are open to a second space, said hollow nanotubes having inside diameters dimensioned to allow impurities to transport therethrough;
    generating an electric field across the nanotubes to facilitate transport of the impurities through the hollow nanotubes; and
    causing the fluid in the first space to transport through the hollow nanotubes into the second space, wherein impurities in the fluid that have been transported into the second space can be collected and separated from said fluid in the first space.

12. The method of claim 11, wherein fluid in the first space is recirculated a plurality of times to provide a plurality of purification passes.

13. The method of claim 11, where the fluid is blood.

14. The method of claim 13, wherein the hollow nanotubes are dimensioned to block constituents of the blood from passing through, but allow smaller-sized impurities to pass through.

15. The method of claim 13, wherein the nanotubes are functionalized to prevent coagulation of the blood.

* * * * *